United States Patent
Fuglsang et al.

(10) Patent No.: US 6,264,925 B1
(45) Date of Patent: Jul. 24, 2001

(54) CELLULOSE BINDING DOMAINS (CBDS) FOR ORAL CARE PRODUCTS

(75) Inventors: Claus Crone Fuglsang, Nivå; Rie Tsuchiya, Birkerød, both of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/288,493

(22) Filed: Apr. 8, 1999

Related U.S. Application Data

(63) Continuation of application No. PCT/DK97/00447, filed on Oct. 13, 1997.

(30) Foreign Application Priority Data

Oct. 11, 1996 (DK) .................................................. 1126/96

(51) Int. Cl.[7] .............................. A61K 7/16; A61K 7/28; A61K 9/20; A61K 9/68
(52) U.S. Cl. .............................. 424/50; 424/48; 424/440; 424/441; 424/464; 424/465; 424/489
(58) Field of Search ............................. 424/49–58, 440, 424/441, 464, 489

(56) References Cited

FOREIGN PATENT DOCUMENTS

| WO 92/06191 | 4/1992 | (WO) . |
|---|---|---|
| WO 93/21331 | 10/1993 | (WO) . |
| WO 93/22341 | 11/1993 | (WO) . |
| WO 95/31533 | 11/1995 | (WO) . |
| WO 95/31566 | 11/1995 | (WO) . |
| 97/29197 * | 8/1997 | (WO) . |
| 97/38669 * | 10/1997 | (WO) . |
| 98/00528 * | 1/1998 | (WO) . |
| 98/00529 * | 1/1998 | (WO) . |
| 99/33957 * | 7/1999 | (WO) . |

OTHER PUBLICATIONS

Tomme et al., (1995) American Chem. Soc. 10:142–161.
Ong et al., (1989) Tibtech 7:239–243.

* cited by examiner

Primary Examiner—Shep K. Rose
(74) Attorney, Agent, or Firm—Elias Lambiris, Esq.

(57) ABSTRACT

The present invention relates to an oral care composition comprising a Cellulose Binding Domain and further ingredient conventionally used in oral care compositions, oral care products, and the use of CBDs for oral care purposes.

7 Claims, 1 Drawing Sheet

CELLULOSE BINDING DOMAINS (CBDS) FOR ORAL CARE PRODUCTS

CROSS-REFERENCE TO RELATED APPLICATIONS

This application is a continuation of PCT/DK97/00447 filed Oct. 13, 1997 which claims priority under 35 U.S.C. 119 of Danish application 1126/96 filed Oct. 11, 1996, the contents of which are fully incorporated herein by reference.

FIELD OF THE INVENTION

The present invention relates to an oral care composition comprising a Cellulose Binding Domain, an oral care product comprising an oral care composition of the invention, and further to the use of a Cellulose Binding Domain for oral care purposes, including prevention of the formation of dental plaque and/or removal of dental plaque.

BACKGROUND OF THE INVENTION

The formation of dental plaque leads to dental caries, gingival inflammation, periodontal disease, and eventually tooth loss. Dental plaque is a mixture of bacteria, epithelial cells, leukocytes, macrophages, and other oral exudate. Said bacteria produce highly branched polysaccharides which together with micro-organisms from the oral cavity form an adhesive matrix for the continued proliferation of dental plaque.

As dental plaque continues to accumulate rock hard white or yellowish deposits arise. These deposits are called calcified plaque, calculus or tartar, and are formed in the saliva from plaque and minerals, such as in particular calcium.

Oral polysaccharides

Oral polysaccharides mainly consist of the adhesive polysaccharides termed "fructans" and "glucans".

Glucans are produced from carbohydrates, such as sucrose introduced into the mouth, e.g. as a food or beverage constituent, by the action of cariogenic micro-organisms, such as *Streptococcus mutans* or *Streptococcus sanguis*, growing in the oral cavity.

The term "glucan" is a general common term covering a number of polysaccharides and includes cellulose, starch, dextran, mutan, pullulan etc.

Oral glucans comprise water-soluble dextran having large portions of a-1,6 glucosidic linkage and as the major component a water-insoluble extra-cellular polysaccharide called "mutan" comprised of a backbone with a-1,3-glycosidic linkages and branches with a-1,6-glycosidic linkages.

Mutan binds to almost any surface such as the surface of teeth, (i.e. hydroxyapatite constituting the hard outer porous layer of the teeth), pellicle, the cell surface of oral micro-organisms as well as to acceptor proteins on the cell of said cariogenic bacteria adhering to the teeth surface.

WO 95/31556 (Unilever) discloses an oral composition comprising the Glucan Binding Domain of glycosyltransferase having specific binding affinity for dextran (being a polysaccharide with mainly α-1,6-glucosidic linkages).

According to WO 95/31556 the Glucan Binding Domain is covalently chemically bound to material having an activity, such as inhibitory effect against the formation of dental plaque. Said material may be an enzyme, such as galactose oxidase (see Example 6 of said PCT application).

A number of Cellulose Binding Domains are known in the art. Peter Tomme et al., (1996), "Cellulose-Binding Domains: Classification and Properties" in "Enzymatic Degradation of Insoluble Carbohydrates", John N. Saddler and Michael H. Penner (Eds.), ACS Symposium Series, No. 618; Ong et al. (1989), TIBTech 7, p. 239–243; and WO 93/21331 described a vast number of Cellulose Binding Domains.

SUMMARY OF THE INVENTION

It is the object of the present invention to provide oral care products which can be used for improving the oral hygiene of humans and animals by effectively preventing the formation of dental plaque and/or removing already deposited dental plaque.

The present inventors have found that Cellulose Binding Domains (CBDs) have an dispersing effect on oral polysaccharides. Consequently, Cellulose Binding Domains are suitable for removing and/or preventing dental plaque.

In the following the abbreviation "CBD" will be used for "Cellulose Binding Domain".

Cellulose Binding Domain (CBD)

A CBD is a polypeptide which has high affinity for or binds to water-insoluble forms of cellulose and chitin, including crystalline forms.

CBDs are found as integral parts of large protein complexes consisting of two or more different polypeptides, for example in hydrolytic enzymes (hydrolases) which typically are composed of a catalytic domain containing the active site for substrate hydrolysis, and a Carbohydrate Binding Domain or Cellulose Binding Domain (CBD) for binding to the insoluble matrix. Such enzymes can comprise more than one catalytic domain and one, two or three CBDs and optionally one or more polypeptide regions linking the CBD(s) with the catalytic domain(s), the latter regions usually being denoted a "linker". Examples of hydrolytic enzymes comprising a CBD are cellulases, xylanases, mannanases, arabinofuranosidases, acetyl esterases and chitinases. CBDs have also been found in algae, e.g. the red alga *Porphyra purpurea* as a non-hydrolytic polysaccharide binding protein, see Peter Tomme et al. "Cellulose Binding Domains: Classification and Properties" in "Enzymatic Degradation of Insoluble Carbohydrates", John N. Saddler and Michael H. Penner (Eds.), ACS Symposium Series, No. 618, 1996. However, most of the known CBDs are from cellulases and xylanases.

In this context, the term "Cellulose Binding Domain" is intended to be understood as defined by Tomme et al., op. cit. This definition classifies more than 120 Cellulose Binding Domains into 10 families (I–X) which may have different functions or roles in connection with the mechanism of substrate binding. However, it is anticipated that new family representatives and additional CBD families will appear in the future.

In the protein complex, typically a hydrolytic enzyme, a CBD is located at the N or C termini or is internal.

A monomeric CBD typically consists of more than about 30 and less than about 250 amino acid residues. For example, a CBD classified in Family I consists of 33–37 amino acid residues; a CBD classified in Family IIa consists of 95–108 amino acid residues; and a CBD classified in Family VI consists of 85–92 amino acid residues. Accordingly, the molecular weight of a monomeric CBD will typically be in the range of from about 4 kD to about 40 kD, and usually below about 35 kD.

CBDs may be useful as a single domain polypeptide (single unit CBD) or as a dimer, a trimer, or a polymer; or as a part of a protein hybrid.

Single Unit Cellulose Binding Domain (single unit CBD)

The term "Single Unit CBD" may also be referred to as "Isolated CBD" or "Separate CBD".

In the context of the present invention a "Single Unit CBD" includes up to the entire part of the amino acid sequence of a CBD-containing enzyme, e.g. a polysaccharide hydrolysing enzyme, being essentially free of the catalytic domain, but retaining the CBD(s).

Thus, in the context of the invention, the entire catalytic amino acid sequence of a cellulolytic enzyme (e.g. a cellulase) or other enzymes comprising one or more CBDs is not to be regarded as a Single Unit CBD.

Typically a Single Unit CBD constitutes one or more CBDs of a polysaccharide hydrolysing enzyme, one or more CBDs of a cellulose binding protein or a protein designed and/or engineered to be capable of binding to cellulosic carbohydrates.

The Single Unit CBD is at least as large as the minimum number of amino acids in the amino acid sequence required to bind to cellulosic carbohydrates.

A Single Unit CBD may also be an amino acid sequence in which the binding and catalytic domain are one and the same.

Cellulases useful for preparation of Cellulose Binding Domains

The techniques used in isolating a cellulase gene are well-known in the art.

In the present context, the term "cellulase" refers to an enzyme which catalyses the degradation of cellulose to glucose, cellobiose, triose and other cello-oligosaccharides.

Preferably, the cellulase is a microbial cellulase, more preferably a bacterial or fungal cellulase.

Examples of bacterial cellulases are cellulases derived from or producible by bacteria from the group consisting of Pseudomonas, Bacillus, Cellulomonas, Clostridium, Microspora, Thermotoga, Caldocellum and Actinomycets such as Streptomyces, Termomonospora and Acidothemus, in particular from the group consisting of *Pseudomonas cellulolyticus, Bacillus lautus, Cellulomonas fimi, Microspora bispora, Termomonospora fusca, Termomonospora cellulolyticum* and *Acidothemus cellulolyticus*.

The cellulase may be an acidic, a neutral or an alkaline cellulase, i. e. exhibiting maximum cellulolytic activity in the acidic, neutral or alkaline range, respectively.

A useful cellulase is an acid cellulase, preferably a fungal acidic cellulase, which is derived from or producible by fungi from the group of genera consisting of Trichoderma, Myrothecium, Aspergillus, Phanaerochaete, Neurospora, Neocallimastix and Botrytis.

A preferred useful acidic cellulase is derived from or producible by fungi from the group of species consisting of Trichoderma viride, Trichoderma reesei, Trichoderma longibrachiatum, Myrothecium verrucaria, Aspergillus niger, Aspergillus oryzae, Phanaerochaete chrysosporium, Neurospora crassa, Neocallimastix partriciarum and Botrytis cinerea.

Another useful cellulase is a neutral or alkaline cellulase, preferably a fungal neutral or alkaline cellulase, which is derived from or producible by fungi from the group of genera consisting of Aspergillus, Penicillium, Myceliophthora, Humicola, Irpex, Fusarium, Stachybotrys, Scopulariopsis, Chaetomium, Mycogone, Verticillium, Myrothecium, Papulospora, Gliocladium, Cephalosporium and Acremonium.

A preferred alkaline cellulase is derived from or producible by fungi from the group of species consisting of *Humicola insolens, Fusarium oxysporum, Myceliopthora thermophila, Penicillium janthinellum* and *Cephalosporium sp.*, preferably from the group of species consisting of *Humicola insolens*, DSM 1800, *Fusarium oxysporum*, DSM 2672, *Myceliopthora thermophila*, CBS 117.65, and *Cephalosporium sp.*, RYM-202.

A preferred example of a native or parent cellulase is an alkaline endoglucanase which is immunologically reactive with an antibody raised against a highly purified ~43 kD endoglucanase derived from *Humicola insolens*, DSM 1800, or which is a derivative of the ~43 kD endoglucanase exhibiting cellulase activity.

Other examples of useful cellulases are variants having, as a parent cellulase, a cellulase of fungal or bacterial origin, e.g. a cellulase derivable from a strain of the fungal genus Humicola, Trichoderma or Fusarium.

The techniques used for isolating a xylanase gene, a mannanase gene, an arabinofuranosidase gene, an acetyl esterase gene or a chitinase gene are also well known in the art.

Isolation of a Cellulose Binding Domain (CBD)

In order to isolate a Cellulose Binding Domain of e.g. a cellulase, several genetic approaches may be used. One method uses restriction enzymes to remove a portion of the gene and then to fuse the remaining gene-vector fragment in frame to obtain a mutated gene that encodes a protein truncated for a particular gene fragment.

Another method involves the use of exonucleases such as Ba131 to systematically delete nucleotides either externally from the 5' and the 3' ends of the DNA or internally from a restricted gap within the gene. These gene deletion methods result in a mutated gene encoding a shortened gene molecule which may then be evaluated for substrate binding ability.

Appropriate substrates for evaluating the binding activity include compounds such as Avicel and cotton fibres.

Once a nucleotide sequence encoding the substrate binding region has been identified, either as cDNA or chromosomal DNA, it may then be manipulated in a variety of ways to fuse it to a DNA sequence encoding the enzyme of interest. The cellulose binding encoding fragment and the DNA sequence encoding the enzyme of interest are then ligated with or without a linker.

The resulting ligated DNA sequence may then be manipulated in a variety of ways to provide for expression. Microbial hosts such as Aspergillus, e.g., *A. niger* and *A. oryzae*, Bacillus, *E. coli* or *S. cerevisiae* are preferred.

In the first aspect the invention relates to an oral care composition comprising a CBD and ingredients conventionally used in oral care compositions.

The CBD may be any CBD, such as a Single Unit CBD of any kind. CBDs specifically contemplated are CBDs isolated from micro-organisms, such as bacteria, filamentous fungi or yeasts, especially CBDs derived from e.g. a strain of Pseudomonas sp. or Clostridlium sp..

In an embodiment of the invention the oral care composition further comprises an enzyme capable of degrading polysaccharides.

In the second aspect the invention relates to an oral care product comprising an oral care composition of the invention.

In the third aspect the invention relates to the use of a CBD for oral care purposes, including preventing the formation of dental plaque and/or removing dental plaque.

DETAILED DESCRIPTION OF THE INVENTION

Figure 1:
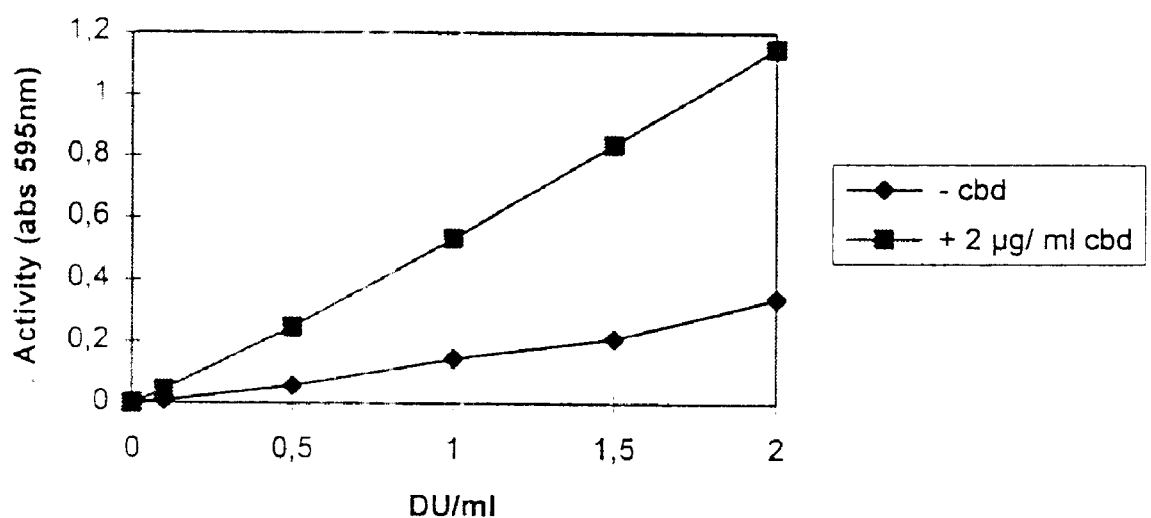
FIG. 1 shows the activity of the combined action of CBDs and dextranase on AZCL-dextran in 0.1 M sodium acetate, pH 5.5.

It is the object of the present invention to provide oral care products which can be used for improving the oral hygiene of humans and animals, by effectively preventing the formation of dental plaque and/or removing already deposited dental plaque.

The present inventors have found that Cellulose Binding Domains (CBDs), known to have affinity for binding specifically to cellulose, disperses polysaccharides. Due to this dispersing effect CBDs is suitable for removing and/or preventing the formation of dental plaque.

This is surprising as a person skilled in the art of dental science would not expect that CBDs have a dental plaque removing and/or preventing effect, as CBDs are generally believed to have no or a lower affinity for oral polysaccharides which do not comprise significant amounts of cellulose (an un-branched polysaccharide of glucose residues joined by β-1,4-linkages).

In the present context "... a lower binding affinity ..." means that the binding affinity of CBDs for none-cellulosic polysaccharides, such as dextran and mutan constituting oral polysaccharides, is lower than the binding affinity for cellulose.

Without being limited to any theory the inventors believe that the dental plaque removing and/or preventing effect of CBDs is due to the dispersion of the oral polysaccharide resulting in dissolution or at least disruption of the polysaccharides of dental plaque. This facilitates the removal of the dental plaque when e.g. brushing the teeth, rinsing the mouth with a mouth wash or the like.

In the first aspect the invention relates to an oral care composition comprising a CBD an further ingredients conventionally used in oral care compositions.

In a preferred embodiment the CBD is a Single Unit CBD as defined above.

Any CBD may be used. Specifically contemplated are CBDs described by Peter Tomme et al. (1996), supra, and the other CBDs described above.

The inventors have also found that CBDs advantageously can be used in combination with an enzyme activity capable of degrading the polysaccharides of dental plaques.

The Action of CBDs

Efficient enzymatic degradation requires a tight interaction between a substrate and an enzyme. Further, it is known that CBDs enhance enzyme activities as the local enzyme concentration on the substrate surface to which it can bind (i.e. mainly cellulosic polysaccharides) is increased (Peter Tomme et al. (1996), supra).

However, it is surprising that CBDs enhance the activity of enzymes acting on substrates to which CBDs are generally believed to have no or a lower affinity towards (i.e. none-cellulosic carbohydrates) than to cellulosic polysaccharides.

Consequently in a preferred embodiment the oral care composition comprises a CBD and an enzyme capable of degrading oral care polysaccharides.

Preferred enzymes are glycosidases capable of hydrolysing glycosidic linkages and hereby capable of degrading oral polysaccharides.

All glycosidases within E.C. 3.2. "Enzyme Nomenclature (1992), Academic Press, Inc.". are contemplated according to the invention and are hereby incorporated by reference.

When combining a CBD with an enzyme capable of degrading oral polysaccharides a synergistic effect is obtained. It is believed that the CBD provide accessibility to the substrate (i.e. the oral polysaccharides) giving the enzyme so to speak access to the substrate and enabling an intimate association and proximity (i.e. a tighter interaction) between the enzyme and it's substrate. This results in a faster degradation of the dental plaque or a render it possible to use less enzyme to obtain the desired result.

In Example 2 the dental plaque preventing effect of CBDs is illustrated. When using CBDs alone or in combination with (a) glycosidase(s) (in Example 2 illustrated with the combination of a dextranase and a glucanase) the a dental plaque preventing effect is shown.

Preferred glycosidases are α-glycosidases, especially α-glycosidases selected from the group of dextranases, mutanases, pullulanases and α-amylases, or mixtures thereof.

The dextranase may the derived from a strain of the genera Penicillium, Paecilomyces, Aspergillus, Fusarium, Spicaria, Verticillium, Helminthosporium and Chaetomium; bacteria of the genera Lactobacillus, Streptococcus, Cellvibrio, Cytophaga, Brevibacterium, Pseudomonas, Corynebacterium, Arthrobacter and Flavobacterium, and yeasts such as *Lipomyces starkeyi*. Specifically contemplated is dextranases derived from a strain of *Paecilomyces lilacinum*.

The mutanase may be derived from a strain of the genera Trichoderma, Streptomyces, Cladosporium, Bacillus, Aspergillus Specifically contemplated is mutanases derived from *T. harzianum*, especially the deposited strain *T. harzianum* CBS 243.71.

The oral care composition may further comprise one or more enzymes, which may be recombinant, selected from the group including oxidases, peroxidases, proteases, lipases, other glycosidases, lipases, esterases, deaminases, ureases and polysaccharide hydrolases, or mixtures thereof.

The oral care composition may further comprise agents adding an additional property to the oral care composition.

Such additional agents include other anti-plaque agents, anti-staining agents, anti-microbial agents, antibodies, antibody fragments, histamins, lactoferins, defensins, magainins, cecropins, other cationic anti-bacteriocins, bacteriocins, microbicides including, but not limited to, triclosan, chlorhexidine, quaternary ammonium compounds, chloroxylenol, chloroxyethanol, thymol, fluoride, antimicrobial cat-ions such as Zn, Sn, Cu.

An oral care composition of the invention may suitably have incorporated an amount of 0.001–10 mg/ml CBD calculated on the basis of final oral care product.

When adding glycosidases to the oral care composition these may constitute from 0.0001% to 20%, preferably 0.001% to 5% of the final oral care product.

In the case of the glycosidase(s) is(are) a dextranase, mutanase, pullulanase, respectively, they may, independent of each other, be added in amounts equivalent to an enzyme activity, calculated as enzyme activity units in the final oral care product, in the range from 0.001 KDU to 1000 KDU/ml, preferably from 0.01 KDU/ml to 500 KDU/ml, especially from 0.1 KDU/ml to 100 KDU/ml for dextranase, and/or from 0.001 MU/ml to 1000 MU/ml, preferably from 0.01 MU/ml to 500 MU/ml, especially from 0.01 MU/ml to 100 MU/ml and from 0.01 MU/ml to 100 MU/ml, for mutanases, and/or in the range from 0.001 KPU to 1000 KPU/ml, preferably from 0.01 KPU/ml to 500 KPU/ml, especially from 0.1 KPU/ml to 100 KPU/ml for pullulanases.

It is preferred that the enzyme(s) is(are) substantially active at temperatures and pHs prevailing in the mouth when using the oral care product of the invention. This normally means that the enzymes should be substantially active between 20° C. and 40° C., and at pHs in the range from pH 4.0 to 8.0.

The term "substantially active" means in the context of the present invention that the enzyme in question has a relative activity above 70%, in particular above 80%, especially above 90% of the activity at the temperature optimum.
Oral care products The invention also relates to oral care products comprising an oral care composition of the invention. The oral care product may have any suitable physical form (i.e. powder, paste, gel, liquid, ointment, tablet etc.).

An "oral care product" can be defined as a product which can be used for maintaining or improving the oral hygiene in the mouth of humans and animals, by preventing formation of dental plaque, removing dental plaque, preventing and/or treating dental diseases etc.

At least in the context of the present invention oral care products do also encompass products for cleaning dentures, artificial teeth and the like.

Examples of such oral care products include toothpaste, dental cream, gel or tooth powder, odontic, mouth washes, pre or post brushing rinse formulations, chewing gum, lozenges, and candy.

Toothpastes and tooth gels typically include abrasive polishing materials, foaming agents, flavouring agents, humectants, binders, thickeners, sweetening agents, whitening/bleaching/ stain removing agents, water, and optionally enzymes.

Mouth washes, including plaque removing liquids, typically comprise a water/alcohol solution, flavour, humectant, sweetener, foaming agent, colorant, and optionally enzymes.

Abrasive polishing material might also be incorporated into the dentifrice product of the invention. According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like.

It is also possible to employ mixtures of these substances.

Dependent on the oral care product the abrasive product may be present in from 0 to 70% by weight, preferably from 1% to 70%. For toothpastes the abrasive material content typically lies in the range of from 10% to 70% by weight of the final toothpaste product.

Humectants are employed to prevent loss of water from e.g. toothpastes. Suitable humectants for use in oral care products according to the invention include the following compounds and mixtures thereof: glycerol, polyol, sorbitol, polyethylene glycols (PEG), propylene glycol, 1,3-propanediol, 1,4-butanediol, hydrogenated partially hydrolysed polysaccharides and the like. Humectants are in general present in from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing the dentifrice product. Thickeners may be present in toothpaste creams and gels in an amount of from 0.1 to 20% by weight, and binders to the extent of from 0.01 to 10% by weight of the final product.

As foaming agent soap, anionic, cationic, non-ionic, amphoteric and/or zwitterionic surfactants can be used. These may be present at levels of from 0% to 15%, preferably from 0.1 to 13%, more preferably from 0.25 to 10% by weight of the final product.

Surfactants are only suitable to the extent that they do not exert an inactivation effect on the present CBDs/enzymes. Surfactants include fatty alcohol sulphates, salts of sulphonated mono-glycerides or fatty acids having 10 to 20 carbon atoms, fatty acid-albumen condensation products, salts of fatty acid amides and taurines and/or salts of fatty acid esters of isethionic acid.

Suitable sweeteners include saccharin.

Flavours, such as spearmint, are usually present in low amounts, such as from 0.01% to about 5% by weight, especially from 0.1% to 5%.

Whitening/bleaching agents include $H_2O_2$ and may be added in amounts less that 5%, preferably from 0.25 to 4%, calculated on the basis of the weight of the final product.

Water is usually added in an amount giving e.g. toothpaste a flowable form.

Further water-soluble anti-bacterial agents, such as chlorhexidine digluconate, hexetidine, alexidine, quaternary ammonium anti-bacterial compounds and water-soluble sources of certain metal ions such as zinc, copper, silver and stannous (e.g. zinc, copper and stannous chloride, and silver nitrate) may also be included.

Also contemplated according to the invention is the addition of compounds which can be used as fluoride source, dyes/colorants, preservatives, vitamins, pH-adjusting agents, anti-caries agents, desensitizing agents etc.

Other essential components used in oral care products and in oral care products of the invention are enzymes. Enzymes are biological catalysts of chemical reactions in living systems. Enzymes combine with the substrates on which they act forming an intermediate enzyme-substrate complex. This complex is then converted to a reaction product and a liberated enzyme which continue its specific enzymatic function.

Enzymes provide several benefits when used for cleansing of the oral cavity. Proteases break down salivary proteins, which are absorbed onto the tooth surface and form the pellicle, the first layer of resulting plaque. Proteases along with lipases destroy bacteria by lysing proteins and lipids which form the structural components of bacterial cell walls and membranes. Dextranase breaks down the organic skeletal structure produced by bacteria that forms a matrix for bacterial adhesion. Proteases and amylases, not only prevents plaque formation, but also prevents the development of calculus by breaking-up the carbohydrate-protein complex that binds calcium, preventing mineralization.

A toothpaste produced from an oral care composition of the invention (in weight % of the final toothpaste) may typically comprise the following ingredients:

| | |
|---|---|
| Abrasive material | 10 to 70% |
| Humectant | 0 to 80% |
| Thickener | 0.1 to 20% |
| Binder | 0.01 to 10% |
| Sweetener | 0.1% to 5% |
| Foaming agent | 0 to 15% |
| Whitener | 0 to 5% |
| Enzymes | 0.0001% to 20% |
| Cellulose Binding Domain | 0.0001% to 1% |

A mouth wash produced from an oral care composition of the invention (in weight % of the final mouth wash product) may typically comprise the following ingredients:

| | |
|---|---|
| 0–20% | Humectant |
| 0–2% | Surfactant |
| 0.0001%–5% | Enzymes |
| 0.0001%–1% | Cellulose Binding Domain |
| 0–20% | Ethanol |
| 0–2% | Other ingredients (e.g. flavour, sweetener active ingredients such as florides). |
| 0–70% | Water |

The mouth wash composition may be buffered with an appropriate buffer e.g. sodium citrate or phosphate in the pH-range 6–7.5.

The mouth wash may be in none-diluted form (i.e. must be diluted before use).

Said enzymes referred to in connection with the specific toothpaste and mouth wash above include glycosidases, preferably α-glycosidases, especially dextranase, mutanase, pullulanase, and α-amylase described above, and optionally other types of enzymes mentioned above known to be used in toothpastes and the like.

Method of Manufacture

The oral care composition and products of the present invention can be made using methods which are common in the oral product area.

Finally the invention relates to the use of a CBD for oral care purposes, such as removing or preventing dental plaque formation in the oral cavity of humans or animals.

In a preferred embodiment the CBD is a Single Unit CBD as defined above.

In a preferred embodiment the use of a CBD is combined with one or more enzyme(s) selected from the above mentioned group of enzymes.

MATERIALS AND METHODS

Materials

Dextranase produced by *Paecilomyces lilacinum* (available from Novo Nordisk A/S).

Mutanase produced by *Trichoderma harzianum* CBS 243.71 (available from Novo Nordisk A/S).

Cellulose Binding Domain purchased from Sigma product no. C1332 AZCL-Dextran purchased from Megazyme, AU Micro-organisms:

*Streptococcus sobrinus* strain CBS 350.71 (or OMZ 176)

*Actinomyces viscosus* DSM 43329

*Fusobacterium nucleatum* subsp. *polymorphum* DSM 20482

Solutions

Britton-Robinson Buffer

Erythrosin B (Sigma)

Equipment

Shaker (Eppndorf Thermomixer, Type 5436)

Chromameter CR-200 (Minolta)

Preparation of Mutan

Mutan is prepared by growing *Streptococcus mutans* CBS 350.71 at pH 6.5, 37° C. (kept constant), and with a aeration rate of 75 rpm in a medium comprised of the following components:

| | |
|---|---|
| NZ-Case | 6.5 g/litre |
| Yeast Extract | 6 g/litre |
| $(NH_4)_2SO_4$ | 20 g/litre |
| $K_2PO_4$ | 3 g/litre |
| Glucose | 50 g/litre |
| Pluronic PE6100 | 0.1% |

After 35 hours, sucrose is added to a final concentration of 60 g/liter to induce glycosyltransferase. The total fermentation time is 75 hours. The supernatant from the fermentation is centrifuged and filtered (sterile). Sucrose is then added to the supernatant to a final concentration of 5% (pH is adjusted to pH 7.0 with acetic acid) and the solution is stirred overnight at 37° C. The solution is filtered and the insoluble mutan is harvested on propex and washed extensively with deionized water containing 1% sodium benzoate, pH 5 (adjusted with acetic acid). Finally, the insoluble mutan is lyophilized and ground.

Methods

Determination of dextranase activity (KDU)

One Kilo Novo Dextranase Unit (1 KDU) is the amount of enzyme which breaks down dextran forming reducing sugar equivalent to 1 g maltose per hour in Novo Nordisk' method for determination of dextranase based on the following standard conditions:

Substrate . . . Dextran 500 (Pharmacia)

Reaction time . . . 20 minutes

Temperature . . . 40° C.

pH . . . 5.4

A detailed description of Novo Nordisk's analytical method (AF 120) is available on request.

Determination of mutanase activity (MU)

One Mutanase Unit (MU) is the amount of enzyme which under standard conditions liberates 1 mmol reducing sugar (calculated as glucose) per minute.

Standard Conditions

Substrate . . . 1.5% mutan

Reaction time . . . 15 minutes

Temperature . . . 40° C.

pH . . . 5.5

A detailed description of Novo Nordisk's analytical method (AF 180/1-GB) is available from Novo Nordisk A/S on request.

Preparation of hydroxyapatite disks (HAP disks)

Hydroxyapatite disks are prepared by compressing 250 mg of hydroxyapatite in a disk die at about 5,900 kg (13,000 lbs) of pressure for 5 minutes. The disks are then sintered at 600° C. for 4 hours.

Assessment of the plaque removing effect

The method used for assessing the plaque removal effect is based on the method described by Kao in JP2250816. According to the present method the hydroxyapatite disks (HAP disks) are coated with a biofilm comprising three strains of oral micro-organisms (*Streptococcus sobrinus, Actinomyces viscosus* and *Fusobacterium nucleatum*).

To test the plaque removing and preventing effect 0.1% Erythrosin B in PBS is used to strain plaque present on the hydroxyapatite disks red. The intensity of the red color (i.e. $a^*$) is measured on a Chromameter CR-200. The max. $a^*$ value is 60. Values below that indicate a less intensive red color (i.e. less plaque present). If the $a^*$-value is determined to zero no red color is present (i.e. no plaque).

EXAMPLES

Example 1

Increased hydrolysis of dextran by adding a CBD

250 µl 0.4% AZCL-dextran in 0.1 M sodium acetate, pH 5.5, was incubated with 250 µl enzyme solution (varying the concentration of *P. lilacinum* dextranase between 0 and 2 DU/ml with and without Cellulose Binding Domain (Sigma). The samples were incubated for 10 minutes at 40° C. before centrifuging the samles for 4 minutes at 15,000 g. 200 µl supernatant was taken out and the absorption at 595 nm was read in a microtiter plate reader.

The result of the test is displayed in FIG. 1.

As can be seen from FIG. 1 a significant enhancement of the dextranase activity was observed when combining the CBD and a dextranase.

Example 2

Plaque Inhibition

Hydroxyapatite disks were sterilised at 180° C. for 2 hours before they were incubated with the sterilised saliva at 37° C. overnight. The hydroxyapatite disks were placed at the bottom of wells of Nunclon™ (4×6 wells, ∅ 150 mm), where three oral bacteria, *Streptococcus sobrinus* CBS 350.71, *Actinomyces viscosus* DSM 43329 *Fusobacterium nucleatum* DSM 20482 were inoculated in Brain heard infusion medium containing 0.2% sucrose (total volume: 2.0 ml). The three oral bacteria were cultivated under anaerobic conditions for 16 hours at 37° C.

After cultivation, the disks were rinsed briefly with PBS and then incubated in a 1 ml 0.1% Erythrosin B in PBS for 1 minute. The Erythrosin B solution was taken out by means of suction and the disks were washed with 2.0 ml PBS for a few minutes. Afterwards the disks were dried in air overnight at room temperature, $a^{561}$ was measured with a Chromameter (Minolta).

The dental plaque preventing effect was tested using the samples shown in Table 1.

TABLE 1

| | SBD µg protein/ml | Mutanase/Dextranase | Average a* |
|---|---|---|---|
| 1 | 0 | 0 | 49 |
| 2 | 96 | 0 | 46 |
| 3 | 0 | 1 MU/ml + 1 kDU/ml | 39 |
| 4 | 48 | 1 MU/ml + 1 kDU/ml | 31 |

As can be seen for the Table above CBDs alone have a dental plaque preventing effect. CBDs in combination with Mutanase and Dextranase give an even more improved dental plaque preventing effect.

What is claimed is:

1. An oral care product comprising a Cellulose Binding Domain and further ingredient conventionally used in oral care compositions, wherein the oral care product is a toothpaste dental cream, gel or tooth powder, odontic, mouth washes, pre- or post brushing rinse formulations, chewing gum, lozenges, or candy.

2. The oral care product of claim 1, wherein the Cellulose Binding Domain is a Single Unit Cellulose Binding Domain.

3. The oral care product of claim 1, wherein the Single Unit Cellulose Binding Domain is a cellulolytic enzyme.

4. The oral care product of claim 1, further comprising one or more enzymes selected from the group consisting of deaminases, esterases, glycosidases, lipases, oxidases, peroxidases, polysaccharide hydrolases, proteases, and ureases.

5. The oral care product of claim 4, wherein the enzymes is an α-glycosidase.

6. The oral care product of claim 5, wherein the enzymes is an α-amylase, dextranase, mutanase, or pullulanase.

7. The oral care product of claim 1, further comprising an anti-plaque agent, anti-staining agent, or anti-microbial agent.

* * * * *